United States Patent
Muroyama et al.

(10) Patent No.: US 8,231,882 B2
(45) Date of Patent: Jul. 31, 2012

(54) MOISTURIZER

(75) Inventors: Koutarou Muroyama, Nishinomiya (JP); Tatsuya Ohara, Kakogawa (JP); Yoshitaka Hirose, Itami (JP); Norio Yamamoto, Kobe (JP); Shinji Murosaki, Nara (JP); Yoshihiro Yamamoto, Itami (JP)

(73) Assignee: House Wellness Foods Corporation, Hyogo (JP)

( * ) Notice: Subject to any disclaimer, the term of this patent is extended or adjusted under 35 U.S.C. 154(b) by 357 days.

(21) Appl. No.: 12/310,073

(22) PCT Filed: Aug. 10, 2006

(86) PCT No.: PCT/JP2006/315873
§ 371 (c)(1),
(2), (4) Date: May 28, 2009

(87) PCT Pub. No.: WO2008/018144
PCT Pub. Date: Feb. 14, 2008

(65) Prior Publication Data
US 2009/0281198 A1    Nov. 12, 2009

(51) Int. Cl.
*A61K 9/00* (2006.01)
(52) U.S. Cl. ............... 424/400; 514/847; 514/777
(58) Field of Classification Search ............ 424/400
See application file for complete search history.

(56) References Cited

U.S. PATENT DOCUMENTS

| 6,056,980 | A | 5/2000 | Unno et al. |
| 7,192,746 | B2 * | 3/2007 | Kubota et al. ............ 435/97 |
| 7,786,093 | B2 * | 8/2010 | Hirose et al. ............ 514/53 |
| 2006/0018867 | A1 * | 1/2006 | Kawasaki et al. ........ 424/70.122 |
| 2009/0257965 | A1 | 10/2009 | Ono et al. |
| 2010/0323044 | A1 | 12/2010 | Ono et al. |

FOREIGN PATENT DOCUMENTS

| GB | 2 420 345 | 5/2006 |
| JP | 4-222594 | 8/1992 |
| JP | 9-299095 | 11/1997 |
| JP | 2004-131403 | 4/2004 |
| JP | 2005-304366 | 11/2005 |
| JP | 2005-343801 | 12/2005 |
| JP | 2005-350454 | 12/2005 |
| JP | 2006-124327 | 5/2006 |
| JP | 2006-219416 | 8/2006 |
| WO | 01/90338 | 11/2001 |
| WO | WO 2006006267 | * 1/2006 |

OTHER PUBLICATIONS

Kraft JN and Lynde CW. Moisturizers: What they are and a practical approach to product selection. Skin Therapy Letters. vol. 10, No. 5. Jun. 2005.*
Buske-Kirschbaum and Hellhammer (Ann. NY Acad. Sci. 992: 231-240; 2003).*
International Search Report issued Nov. 10, 2006 in the International (PCT) Application of which the present application is the U.S. National Stage.
Supplementary European Search Report issued Aug. 25, 2009 in European Application No. EP 06 78 2659.

* cited by examiner

*Primary Examiner* — David J Blanchard
*Assistant Examiner* — Devang Thakor
(74) *Attorney, Agent, or Firm* — Wenderoth, Lind & Ponack, L.L.P.

(57) ABSTRACT

The present invention provides a moisturizer comprising, as an active ingredient, a saccharide having 3-O-α-D-glucopyranosyl-D-glucose as a structural unit. The moisturizer of the present invention improves the water retention capacity of the stratum corneum, and is useful for prevention and improvement of rough skin.

3 Claims, 1 Drawing Sheet

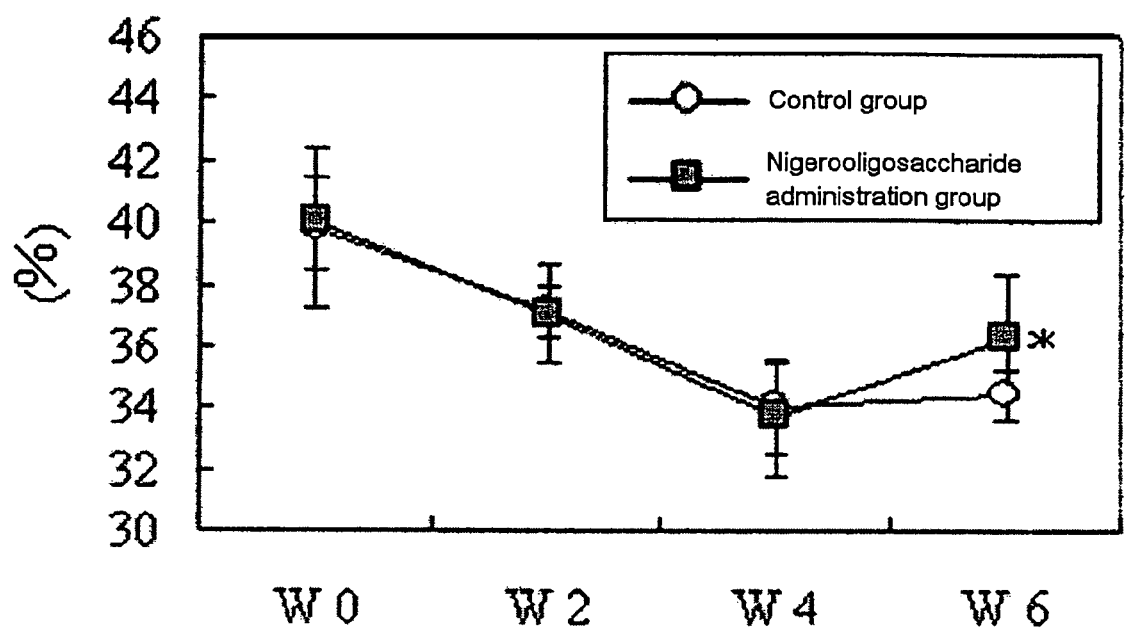

MOISTURIZER

This application is a U.S. national stage of International Application No. PCT/JP2006/315873 filed Aug. 10, 2006.

TECHNICAL FIELD

The present invention relates to a moisturizer, in more detail, a moisturizer comprising, as an active ingredient, a saccharide having 3-O-α-D-glucopyranosyl-D-glucose as a structural unit.

BACKGROUND ART

Human skin is covered with the stratum corneum, which is a thin biological protective membrane. This stratum corneum exposed to the external world allows us to live in the dry atmosphere without losing water. The stratum corneum is thin and supple, and contributes to maintenance of healthy skin by preventing loss of body water. Healthy skin is generally said to have a water content of 10 to 20%.

However, aging, change of seasons, etc. may impair normal system for controlling the water content in the stratum corneum, causing rough skin or serious skin problems. Conventionally, in order to improve the water retention capacity of the stratum corneum and prevent rough skin, polyhydric alcohols such as glycerol, hyaluronic acid, chondroitin, collagen, a mucopolysaccharide, etc. have been used as a moisturizer (see JP-A No. 2001-89381, JP-A No. 2002-145753 and JP-A No. 2005-314402). In particular, a polyhydric alcohol, which has also antiproliferative action on bacteria and has less skin irritation, is widely used as a moisturizing component in cosmetics. However, the moisturizing action of each of the above components, such as polyhydric alcohol, hyaluronic acid, chondroitin, collagen, a mucopolysaccharide, etc. is relatively of short duration, and is not continuously beneficial in improvement or prevention of rough skin. In addition, a feeling of greasiness or hot flashes brought by blending a large quantity of polyhydric alcohol, a mucopolysaccharide, etc. into a skin external agent has also been pointed out as a problem. Cosmetics containing saccharides such as panose for the purpose of solving these problems have been known (see JP-A No. 6-219935 and JP-A No. 2005-89356).

DISCLOSURE OF THE INVENTION

Problem to be Solved by the Invention

In view of the situation, an object of the present invention is to provide a moisturizer which has a beneficial moisturizing effect. In particular, an object of the present invention is to provide a moisturizer which exhibits a moisturizing effect by oral administration (internal use).

Means for Solving the Problem

In order to solve the above-described problem, the present inventors conducted intensive investigations and found that a saccharide having 3-O-α-D-glucopyranosyl-D-glucose as a structural unit exhibits a beneficial moisturizing effect. They have carried out further investigations based on the finding, and completed the present invention.

Namely, the present invention relates to:

(1) a moisturizer comprising, as an active ingredient, a saccharide having 3-O-α-D-glucopyranosyl-D-glucose as a structural unit;

(2) the moisturizer according to the above (1), wherein the saccharide is a linear oligosaccharide;

(3) the moisturizer according to the above (1), wherein the saccharide is a nigerooligosaccharide comprising at least one of nigerose, nigerosyl glucose and nigerosyl maltose;

(4) the moisturizer according to any one of the above (1) to (3), which is for oral administration;

(5) a method for moisturizing skin, comprising administering an effective dose of saccharide having 3-O-α-D-glucopyranosyl-D-glucose as a structural unit to a human who needs moisturization of skin; and (6) a use of a saccharide having 3-O-α-D-glucopyranosyl-D-glucose as a structural unit for producing a moisturizer.

Effect of the Invention

The moisturizer of the present invention exerts a beneficial moisturizing effect in prevention or improvement of various cutaneous symptoms including wrinkles, sagging, tensioned skin, speckles and dullness, when administered orally, or applied directly to skin.

BRIEF DESCRIPTION OF DRAWINGS

FIG. 1 shows the temporal change of the water content in the stratum corneum (%) of the nigerooligosaccharide administration group and the control group in Test Example 1.

BEST MODE FOR CARRYING OUT THE INVENTION

The active ingredient of the moisturizer relating to the present invention is a saccharide having 3-O-α-D-glucopyranosyl-D-glucose as a structural unit, and examples of the saccharide include nigerooligosaccharides. The nigerooligosaccharide means an oligosaccharide comprising an α-1,3 glucosidic bond and having a degree of glucose polymerization of 2 or more, and includes not only an oligosaccharide exclusively comprising an α-1,3 glucosidic bond, but also an oligosaccharide comprising an α-1,3 glucosidic bond and other bonds. Preferable examples of the nigerooligosaccharide include, in particular, linear nigerooligosaccharides such as nigerose, nigerosyl glucose and nigerosyl maltose represented by the following formulae. These may be used alone, in combination of two or more, or as a carbohydrate mixture containing other components also.

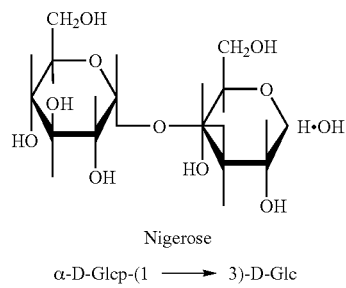

Nigerose

α-D-Glcp-(1 ⟶ 3)-D-Glc

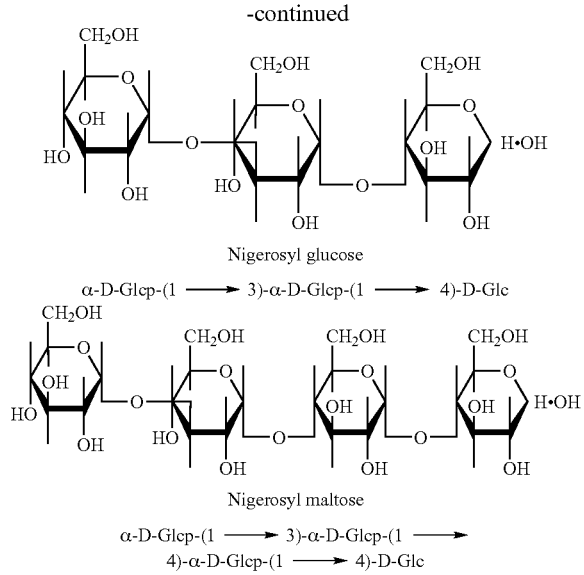

Nigerosyl glucose

α-D-Glcp-(1 ⟶ 3)-α-D-Glcp-(1 ⟶ 4)-D-Glc

Nigerosyl maltose

α-D-Glcp-(1 ⟶ 3)-α-D-Glcp-(1 ⟶ 4)-α-D-Glcp-(1 ⟶ 4)-D-Glc

The saccharide having 3-O-α-D-glucopyranosyl-D-glucose as a structural unit, the saccharide to be used in the present invention, can be easily prepared in accordance with a method known per se. Specifically, for example, nigerooligosaccharide, which is preferable as the saccharide, can be prepared by the following known methods. For example, a method of preparing nigerooligosaccharide by hydrolyzing a substrate such as nigeran and elsinan, using an enzyme, an acid, etc., is suggested in M. Stacey and J. M. Webber: Methods in Carbohydrate Chemistry, I, 339-341, AcademicPress (1962). Moreover, a method of preparing nigerose through known α-glucosidase-catalyzed transglycosylation and condensation reaction is also known (see also Kenichi KANAYA, et al., Japan Society for Bioscience, Biotechnology and Agrochemistry, 53, 385-390 (1979) and H. FUJIMOTO, et al., Agric. Biol. Chem., 52, 1345-1351 (1988), etc.). Further, JP-A No. 3-22958 discloses a method of preparing nigerose by reacting starch hydrolysate with cyclodextrin glucanotransferase. In addition, JP-A No. 7-59559 discloses a method of preparing nigerooligosaccharide by reaction of a substrate containing polysaccharide or oligosaccharide each comprising an α-1,4 glucosidic bond with a glycosyltransferase which forms an α-1,3 glucosidic bond. Specifically, the glycosyltransferase may be a glycosyltransferase prepared by cultivating the fungus of the genus *Acremonium* producing a glycosyltransferase which forms an α-1,3 glucosidic bond, for example, *Acremonium* sp. S4G13 (FERM BP-4373), in accordance with a conventional method. The nigerooligosaccharide used in the present invention can be prepared by any of the above-mentioned methods, but the present invention is not limited thereto. However, the most economical in the known methods so far is probably the method disclosed in the above-mentioned JP-A No. 7-59559, comprising the use of the glycosyltransferase (nigerooligosaccharide producing enzyme). The nigerooligosaccharide prepared in accordance with this method is preferably used in the present invention also.

The moisturizer of the present invention may be orally administered or topically applied to skin in a direct way. In oral administration, a daily dose of the saccharide as an active ingredient may be about 4 mg to 40 g, preferably about 10 mg to 20 g, more preferably about 50 mg to 10 g for an adult weighing about 60 kg although it depends on the sex, age, weight and conditions (symptoms) of the subjects to be administered. When directly applied to skin, a preferable daily dose of the saccharide as an active ingredient is usually about 0.1 to 25 mg, preferably about 0.2 to 10 mg per 10 $cm^2$ of the application site although it may be suitably selected depending on the skin area to be treated. The above daily dose to be administered or applied may be administered or applied in a single dose or divided multiple doses.

In oral administration (internal use), the moisturizer of the present invention may be a solid pharmaceutical preparation, such as powder, a granule, a pill, a tablet, and a capsule, or a liquid such as a syrup. In the production of these pharmaceutical preparations, a carrier or additive suitable for the formulation can be used. Examples of the carrier or additive include an excipient (sodium polyacrylate, calcium polyacrylate, carboxymethylcellulose, lactose, dextrin, cornstarch, crystalline cellulose, saccharose, sodium chloride, glucose, urea, starch, calcium carbonate, kaolin, silicic acid, potassium phosphate, etc.), a lubricant (magnesium stearate, sucrose fatty acid ester, glycerine fatty acid ester, purified talc, polyethylene glycol, etc.), a disintegrant (calcium carboxymethylcellulose, anhydrous dibasic calcium phosphate, sodium carboxymethylcellulose, low substituted hydroxypropylcellulose, dry starch, sodium alginate, agar powder, sodium hydrogencarbonate, calcium carbonate, etc.), a binder (hydroxypropylcellulose, liquid gum arabic, water, ethanol, propanol, simple syrup, dextrose in water, starch in water, gelatin in water, carboxymethylcellulose, methylcellulose, polyvinyl pyrrolidone, etc.), a solubilizer (gum arabic, polysorbate 80, etc.), an absorption enhancer (sodium lauryl sulfate etc.), a buffering agent (phosphate buffer solution, acetate buffer solution, borate buffer solution, carbonate buffer solution, citrate buffer solution, tris buffer solution, etc.), a preservative (methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, disodium edetate, etc.), a thickener (propylene glycol, glycerol, hydroxyethyl cellulose, hydroxypropyl cellulose, polyvinyl alcohol, polyethylene glycol, etc.), a stabilizer (sodium hydrogensulfite, sodium thiosulfate, sodium edetate, sodium citrate, ascorbic acid, dibutyl hydroxytoluene, etc.), or a pH adjustor (hydrochloric acid, sodium hydroxide, phosphoric acid, acetic acid, etc.).

The moisturizer of the present invention may also be contained in cosmetics. Examples of the cosmetics include cleansing preparations such as body wash, hand wash and face wash; skin-care preparations such as lotion, milky lotion and cream; make-up preparations such as foundation, under makeup base and face powder; etc. The amount of the blended moisturizer of the present invention in the cosmetics is not particularly limited, but usually, the preferable amount of saccharide as an active ingredient is about 0.1 to 25% (W/W) and more preferably 0.2 to 10% (W/W) to the total amount of the cosmetics.

EXAMPLE

Hereinafter, the present invention will be illustrated by Test Examples and Examples, but it is not limited thereto.

Test Example 1

A high-purity nigerooligosaccharide (nigerose: 19.8%, trisaccharide fraction mainly containing nigerosyl glucose: 36.5%, tetra- and higher saccharide fraction mainly containing nigerosyl maltose: 40.2%, and glucose: 3.5%) made by Nihon Shokuhin Kako Co., Ltd. was added to a powder feed product (CE-2 made by CLEA Japan, Inc.) so that the nigerooligosaccharide accounted for 3% by weight as a final concentration, and mixed.

For 1 week of preliminary rearing before the start of the test, 7-week-old hairless mice (HR-1, female, supplied by Japan SLC, Inc.) were fed with CE-2 powder feed and water ad libitum. The mice were grouped based on body weight (8 mice in each group). One group was fed with the above-prepared feed containing nigerooligosaccharide, and the other group, as a control group, was fed with CE-2 powder feed not containing nigerooligosaccharide for 6 weeks.

Every 2 weeks after the grouping, the skin on the right side and the left side in the area from the center of the back to the lower body (from lower back to buttocks) were alternately measured 5 times each (10 times in total) with a skin moisture analyzer (Moisture Checker MY-808S made by Scalar Corp.). After exclusion of 2 highest values and 2 lowest values, the mean of the other 6 values was determined as the water content in the stratum corneum (%) of the individual. The mean±SD (standard deviation) of each group was calculated from the above-obtained water contents in the stratum corneum of individuals in the group. FIG. 1 shows the temporal change thereof.

FIG. 1 clearly shows that there was no difference between the nigerooligosaccharide administration group and the control group until Week 4, but that the water content in the stratum corneum of the administration group was significantly improved at Week 6 in comparison with that of the control group.

Test Example 2

The high-purity nigerooligosaccharide prepared in the Test Example 1 was dissolved in distilled water to give a test liquid with a final concentration of 3%. A skin measuring 2 cm by 1.5 cm in the area from lower back to buttock on the left side of each of five 12-week-old hairless mice was determined as a test site. The test liquid in an amount of 10 μL was applied dropwise to the test site, spread within the test site with a finger covered with plastic wrap, and held as it is (with the plastic wrap in contact with the skin) for 1 minute. Meanwhile, distilled water in an amount of 10 μL was applied to a control test site measuring 2 cm by 1.5 cm in the area from lower back to buttock on the right side of each of the same mice. This operation was performed twice a day (in the morning and evening) for three consecutive days. Before the first application on Day 1, and on the day after Day 3 when the last application was performed, the right and the left test sites were measured with the skin moisture analyzer mentioned in the Test Example 1. Each site was measured 5 times, and the mean was determined as the water content in the stratum corneum (%) of the test site. The amount of change in the water content in the stratum corneum was obtained by subtracting the value measured before application from that measured after application. Table 1 shows the water content in the stratum corneum in each test site of 5 individuals, the amount of change thereof, and the mean±SD with respect to each test site. Statistical analysis was conducted by the paired t-test. The * in the table indicates a significant difference with probability less than 5% from the control site.

TABLE 1

|  |  | Individual mouse No. |  |  |  |  | Mean ± SD of change |
|---|---|---|---|---|---|---|---|
|  |  | 1 | 2 | 3 | 4 | 5 |  |
| Water content in stratum corneum (%) in the right side (Control) | Before | 41.42 | 36.70 | 35.02 | 38.36 | 39.88 |  |
|  | After | 35.68 | 33.38 | 34.40 | 37.02 | 35.40 |  |
|  | Change | −5.74 | −3.32 | −0.62 | −1.34 | −4.48 | −3.10 ± 2.13 |
| Water content in stratum corneum (%) in the left side (3% nigerooligosaccharide) | Before | 41.96 | 34.94 | 34.40 | 38.50 | 36.64 |  |
|  | After | 37.92 | 33.54 | 34.08 | 37.30 | 36.18 |  |
|  | Change | −4.04 | −1.40 | −0.32 | −1.20 | −0.46 | −1.48 ± 1.50* |

Table 1 clearly shows that the decrease in the water content in the stratum corneum of the site treated with the nigerooligosaccharide was significantly smaller in comparison with that of the control site.

Test Example 3

As long as 24 hours after the application on Day 3 in the Test Example 2, the same mice were used here. A piece of absorbent cotton (4×4 cm) containing 3 mL of water was placed on each test site in the area from the center of the back to the lower body (from lower back to buttocks), and held for 3 minutes. Immediately after the water was wiped off with a dry cloth, each test site was alternately measured for the water content in the stratum corneum (%) 7 times each. After exclusion of the highest value and the lowest value, the mean of the other 5 values was determined as the water content in the stratum corneum (%) of the individual. Table 2 shows the water content in the stratum corneum in each test site of 5 individuals, and the mean±SD with respect to each test site. Statistical analysis was conducted by the paired t-test. The * in the table indicates a significant difference with probability less than 5% from the control site.

TABLE 2

|  | Individual mouse No. |  |  |  |  | Mean ± SD |
|---|---|---|---|---|---|---|
|  | 1 | 2 | 3 | 4 | 5 |  |
| Water content in stratum corneum (%) in the right side (Control) | 43.98 | 37.98 | 39.58 | 45.62 | 45.06 | 42.44 ± 3.44 |
| Water content in stratum corneum (%) in the left side (3% nigerooligosaccharide) | 44.26 | 41.50 | 48.04 | 45.80 | 47.38 | 45.40 ± 2.62* |

Table 2 clearly shows that the water content in the stratum corneum of the site treated with the nigerooligosaccharide was significantly higher in comparison with that of the control site. Therefore, the nigerooligosaccharide proved to remarkably raise the water retention capacity of the stratum corneum.

Example 1

The ingredients were well mixed in the amounts described in the following Table 3, and the mixture was compressed into tablets each weighing 5 g and containing 700 mg of the moisturizer of the present invention.

TABLE 3

| Ingredient | Amount (% by weight) |
| --- | --- |
| Nigerooligosaccharide | 14 |
| Lactose | 81 |
| Crystalline cellulose | 1 |
| Talc | 4 |

Example 2

A cream preparation containing the ingredients in the following Table 4 in each predetermined amount was produced in the usual manner.

TABLE 4

| Ingredient | Amount (% by weight) |
| --- | --- |
| Nigerooligosaccharide | 2 |
| Polyethylene glycol | 2 |
| Self-emulsifying glyceryl monostearate | 5 |
| Cetyl alcohol | 4 |
| Squalane | 6 |
| Triglyceryl 2-ethylhexanoate | 6 |
| 1,3-butylene glycol | 7 |
| L-histidine | 3 |
| Purified water | q.s. to 100 |

INDUSTRIAL APPLICABILITY

The present invention provides a moisturizer which improves the water retention capacity of the stratum corneum and is useful for prevention and improvement of rough skin.

The invention claimed is:

1. A method for moisturizing skin, comprising orally administering a saccharide having 3-O-α-D-glucopyranosyl-D-glucose as a structural unit to a human who needs moisturization of skin in an amount effective to increase moisturization of the skin, wherein the skin is disease-free.

2. The method according to claim 1, wherein the saccharide is a linear oligosaccharide.

3. The method according to claim 1, wherein the saccharide is a nigerooligosaccharide comprising at least one of nigerose, nigerosyl glucose and nigerosyl maltose.

* * * * *